United States Patent [19]

Hostettler et al.

[11] 4,434,178
[45] Feb. 28, 1984

[54] ANTIPERSPIRANTS

[75] Inventors: Hans U. Hostettler, Arlesheim; Horst Pauling, Bottmingen, both of Switzerland

[73] Assignee: Hoffman-La Roche, Inc., Nutley, N.J.

[21] Appl. No.: 306,696

[22] Filed: Sep. 29, 1981

[30] Foreign Application Priority Data

Oct. 3, 1980 [CH] Switzerland .......................... 7403/80

[51] Int. Cl.³ ...................... A01N 55/02; A61K 31/28
[52] U.S. Cl. .................................... 424/287; 260/414; 260/448 AD; 424/245; 546/5
[58] Field of Search ............ 260/448 AD, 414; 546/5; 424/287, 245

[56] References Cited

U.S. PATENT DOCUMENTS

| | | | |
|---|---|---|---|
| 2,801,190 | 7/1957 | Orthner et al. | 260/448 AD X |
| 2,844,551 | 7/1958 | Orthner et al. | 260/448 AD X |
| 2,913,468 | 11/1959 | Rinse | 260/448 AD X |
| 2,932,659 | 4/1960 | Orthner | 260/448 AD X |
| 2,948,743 | 8/1960 | Rinse | 260/448 AD X |
| 3,214,450 | 10/1965 | Michaels | 260/414 |
| 3,214,451 | 10/1965 | Michaels | 260/414 |
| 3,322,739 | 5/1967 | Hagemeyer et al. | 260/448 AD |
| 3,652,623 | 3/1972 | Washio et al. | 260/448 AD |
| 3,865,857 | 2/1975 | Suzuki et al. | 260/414 X |
| 3,880,901 | 4/1975 | Turner | 260/448 AD |
| 3,988,333 | 10/1976 | Suzuki et al. | 260/414 X |
| 4,055,634 | 10/1977 | Brenner et al. | 260/448 AD X |

FOREIGN PATENT DOCUMENTS 1162853 9/1958 France .
806182 12/1958 United Kingdom .
831346 3/1960 United Kingdom .

*Primary Examiner*—Helen M. S. Sneed
*Attorney, Agent, or Firm*—Jon S. Saxe; George M. Gould; John J. Maitner

[57] ABSTRACT

Aluminum compounds containing organic groups of the formula

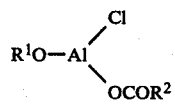

when $R^1$ and $R^2$ are as hereinafter set forth are disclosed as having activity as antiperspirants. Antiperspirant compositions containing one or more of these compounds as transpiration-inhibiting active ingredients and methods for preparing the compounds are also disclosed.

14 Claims, No Drawings

ANTIPERSPIRANTS

BRIEF SUMMARY OF THE INVENTION

The invention relates to aluminum compounds containing organic groups of the formula

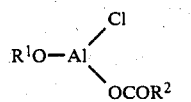

wherein $R^1$ and $R^2$ are as hereinafter set forth, having transpiration-inhibiting activity.

In another aspect, the invention relates to antiperspirant compositions.

DETAILED DESCRIPTION OF THE INVENTION

The invention is directed to aluminum compounds containing organic groups of the formula

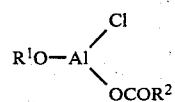

wherein
$R^1$ is $C_{1-18}$-alkyl,
$C_{2-18}$-alkoxyalkyl, phenoxy-$C_{1-6}$-alkyl, phenyl or phenyl substituted with $C_{2-6}$-alkoxycarbonyl and
$R^2$ is $C_{1-15}$-alkyl; phenyl or phenyl substituted with halogen, $C_{1-4}$-alkyl, $C_{1-4}$-alkoxy, $C_{2-6}$-alkanoyloxy and/or $C_{2-6}$-alkoxycarbonyl; phenyl-$C_{1-4}$-alkyl; or pyridyl,
in monomeric, oligomeric or polymeric form.

The compounds of formula I have transpiration-inhibiting activity and are especially suitable as active ingredients for antiperspirant compositions.

The term "alkyl" as used herein denotes not only straight-chain but also branched-chain alkyl groups. The same meaning also applies to the term alkyl when used in connection with alkoxyalkyl, phenoxyalkyl, phenyl substituted with alkoxycarbonyl, phenyl substituted with alyl, alkoxy, alkanoyloxy and/or alkoxycarbonyl, and phenylalkyl. The term term "halogen" denotes fluorine, chlorine, bromine and iodine. When two or more substituents are present in a substituted phenyl group, the substituents can be the same or different.

In certain of the compounds of formula I there are present asymmetric carbon atoms and, accordingly, such compounds can exist as optical antipodes. Formula I is therefore intended to include these possible isomeric forms as well as the racemates.

Among the compounds within the scope of formula I which are suitable for use in this invention are those in which $R^1$ is $C_{1-18}$-alkyl, e.g. methyl, ethyl, n-propyl, isopropyl, n-butyl, isobutyl, sec.butyl, tert.-butyl, n-pentyl, isopentyl, neopentyl, n-hexyl, n-heptyl, n-octyl, n-nonyl, n-decyl, n-undecyl, n-dodecyl, n-tetradecyl, n-hexadecyl and n-octadecyl. Preferred compounds are those where the alkyl group $R^1$ is ethyl.

If $R^1$ denotes phenoxy-$C_{1-6}$-alkyl, the preferred group is 2-phenoxyethyl.

If $R^1$ denotes phenyl substituted with $C_{2-6}$-alkoxycarbonyl, the preferred group is 4-ethoxycarbonylphenyl.

Examples of $R^2$ as $C_{1-15}$-alkyl are the $C_{1-15}$-alkyl groups listed above for $R^1$. The alkyl group $R^2$ is preferably straight-chain.

If $R^2$ denotes phenyl-$C_{1-4}$-alkyl, the preferred group is benzyl.

If $R^2$ denotes pyridyl, then this is preferably 3-pyridyl.

Formula I preferably contains not more than 30 carbon atoms. When $R^1$ or $R^2$ denotes a long-chain alkyl group, i.e. an alkyl group with a number of carbon atoms falling in the upper range of the number of carbon atoms given, then $R^2$ or $R^1$, respectively, is preferably a short-chain alkyl group, (i.e. an alkyl group with a number of carbon atoms falling in the lower range of the number of carbon atoms given.

$R^1$ is preferably $C_{1-18}$-alkyl or phenoxy-$C_{1-6}$-alkyl, especially ethyl.

$R^2$ is preferably $C_{1-15}$-alkyl, phenyl, substituted phenyl or phenyl-$C_{1-4}$-alkyl, especially phenyl.

Especially preferred compounds of formula I are:

Chloro-ethoxy-benzoato-aluminum,
chloro-ethoxy-myristato-aluminum,
chloro-(2-phenoxy-ethoxy)-benzoato-aluminum and
chloro-ethoxy-phenylacetoato-aluminum.

The compounds of formula I can be prepared according to one of the following processes.

(A) Reacting a compound of the formula

wherein
$R^1$ is as described above and
$R^3$ L is $C_{2-8}$-alkyl,
with an acid of the formula

wherein $R^2$ is as described above.

(B) Reacting a compound of the formula

wherein $R^2$ and $R^3$ are as described above, with an alcohol or phenol of the formula

wherein $R^1$ is as described above.

(C) Reacting a compound of the formula

wherein $R^1$, $R^2$ and $R^3$ are as described above with hydrogen chloride.

(D) Reacting a compound of the formula $(R^1O)_2AlCl$      VII wherein $R^1$ is as described above with a compound of the formula $(R^2COO)_2AlCl$      VIII wherein $R^2$ is as described above.

(E) Reacting a compound of the formula $(R^1O)_3Al$      IX wherein $R^1$ is as described above with a compound of the formula $Al(OCOR^2)_3$      X wherein $R^2$ is as described above, and with aluminum trichloride.

(F) Reacting a compound of the formula $R^1OMe$      XI wherein
$R^1$ is as described above and
Me is an alkali metal, preferably sodium or potassium,
with a compound of the formula $MeOCOR^2$      XII wherein $R^2$ and Me are as described above, and with aluminum trichloride.

(G) Reacting a compound of the formula $(R^3)_2AlCl$      XIII wherein $R^3$ is as described above,
with a compound of formula III and a compound of formula V, as described above.

The above processes can conveniently be represented by the following Reaction Scheme:

Reaction Scheme

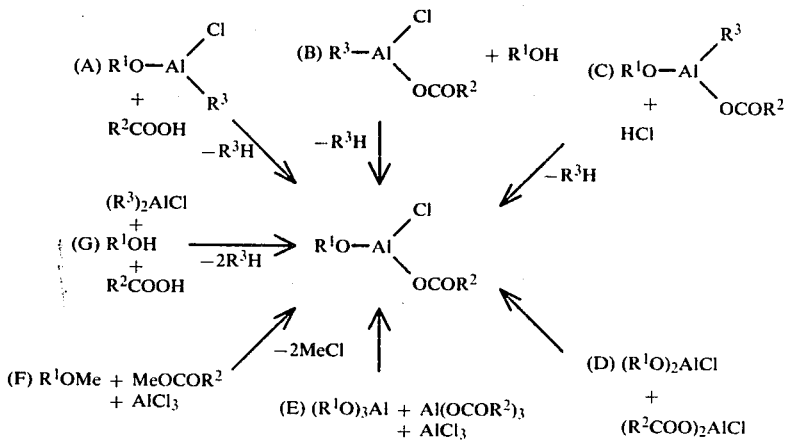

Processes (A), (B), (C) and (G) involve the elimination of the strongly nucleophilic alkyl group $R^3$ from the respective aluminum atom and simultaneous elimination of the proton of the compound of formula III [process (A)] or V [process (B)], of hydrogen chloride [process (C)] and of the compounds of formulae III and V [process (G)] with the formation of a hydrocarbon of the formula $R^3H$. Such reactions generally proceed rapidly and quantitatively, so that conveniently stoichiometric amounts of the starting materials are used. Since the hydrocarbons of the formula $R^3H$ formed can be readily separated, these reactions normally proceed, when pure starting materials are used, in one step to analytically pure compounds of formula I, which generally do not require a separate purification.

Processes (D) and (E) are disproportionation reactions. By warming a mixture of the starting materials, preferably in stoichiometric amounts and conveniently in a solvent or in the form of a melt, the groups situated on the aluminum atoms are interchanged with the formation of the desired compounds of formula I.

Process (F) is a condensation reaction. According to this process there are also conveniently used stoichiometric amounts of the starting materials and this normally yields, when pure starting materials are used, in one step analytically pure compounds of formula I which require no separate purification.

Suitable solvents for carrying out the above processes are non-protonic solvents, e.g. aliphatic, alicyclic or aromatic hydrocarbons such as n-hexane, cyclohexane, benzene, and the like, ethers and ether-like compounds, e.g. diethyl ether and dioxan, and halogenated hydrocarbons such as methylene chloride and chlorobenzene.

The reaction temperatures can vary over a wide range, e.g., $-20°$ C. and $100°$ C., and preferably between $0°$ C. and $50°$ C. The reactions are generally carried out under normal pressure.

Since the starting materials of formulae II, IV, VI and XIII, i.e. those starting materials which have aluminum-carbon bonds, are as a rule very sensitive to hydrolysis or oxidation, the reactions in accordance with processes (A), (B), (C) and (G) are carried out under conditions which are as far as possible anhydrous and air-free. Therefore, the reactions are conveniently carried out in anhydrous solvents and in dry protective gas atmospheres, e.g. under nitrogen or argon.

Isolation of the compounds of formula I is carried out using conventional techniques.

Processes (A) and (B) are preferred.

The compounds of formulae II, III, IV, V, VI, VII, VIII, IX, X, XI, XII and XIII used as starting materials are either known or can be prepared according to known methods.

As in the case of many known aluminum compounds, the aluminum atom in the compounds of formula I in accordance with the invention can also form, with the aid of so-called secondary valency bonds, spatial structures in which the aluminum atom has higher coordination numbers than 3, e.g. 4 or 6. The resulting complex structures usually have no uniform molecular weight, so that the compounds can exist, depending on the steric or electronic factors, as oligomers, e.g. dimers, trimers or tetramers, or even as polymers. Consequently, the compounds can exist as mixtures of several of such forms, which are either amorphous solids, often with high melting or decomposition points or intervals, or glassy-resinous substances. For this reason the compounds in many cases cannot be distilled or recrystallized. Of course, as stated above, when pure starting materials are used compounds of formula I are often obtained in an analytically pure state. In view of the foregoing, formula I is intended to include not only those compounds which exist in monomeric form, but also those compounds which exist in oligomeric or polymeric form, and mixtures of such compounds.

Formula I is intended to include not only those compounds which exist in monomeric form, but also those compounds which exist in oligomeric or polymeric form, and mixtures of such compounds.

The compounds of formula I have transpiration-inhibiting activity. They can accordingly be formulated to give a wide variety of compositions. The antiperspirant compositions of this invention contain an effective amount of at least one compound of formula I, as defined above, as well as cosmetically acceptable carrier materials or other cosmetically-effective adjuvants. The antiperspirant compositions are e.g. in the form of powders, sticks, gels, creams, solutions, sprays or aerosols. These compositions are prepared by conventional procedures known to those skilled in the art.

Examples of carrier materials present in the antiperspirant compositions of the present invention include solvents such as alcohols, e.g. ethanol and isopropanol, water, hydrocarbons, e.g. n-hexane and n-heptane, chlorinated hydrocarbons, e.g. methylene chloride, ethers and ether-like compounds, e.g. dimethyl ether, diethyl ether, tetrahydrofuran, dioxan and 6-acetoxy-2,4-dimethyl-1,3-dioxan, and the like. Examples of solid carrier materials include talc, microcrystalline cellulose and stearyl alcohol, and the like. Examples of liquid carrier materials include isopropyl myristate, silicone oil, and the like. Dispersing agents which can be used in this invention are amorphous silicon dioxide and magnesium stearate; and the like. Thickening agents which can be used in this invention are cellulose polyalkyl ethers. Carrier gases useful in the antiperspirant compositions of the invention include ethers, e.g. dimethyl ether, low-boiling, liquified alkanes, optionally substituted with halogen, e.g. n-propane, n-butane, isobutane, dichlorodifluoromethane, trichlorofluoromethane and dichlorotetrafluoroethane as well as mixtures thereof.

Examples of other cosmetic adjuvants are materials for increasing the skin metabolism or the skin elasticity, such as panthenol and its lower alkyl ethers, e.g. the ethyl ether, bactericidal substances, e.g. quaternary ammonium compounds, other types of transpiration-inhibiting agents, deodorizing agents and perfumes.

The antiperspirant compositions of the invention preferably contain between about 1 and 30 percent by weight, more preferably between about 2 and 20 percent by weight of the active compound or mixtures of active compounds of formula I.

The antiperspirant compositions of this invention are prepared by mixing at least one active ingredient of formula I with a carrier material and, if desired, with other cosmetically-effective adjuvents. The mixing can be carried out in one step or several steps and in a manner which is conventional in cosmetic industry.

The antiperspirant compositions of this invention are used by applying an effective amount of the composition to the area to be treated. This application can be carried out in a conventional manner, e.g. by rubbing-in or spraying.

The following Examples illustrate the invention in more detail:

I. Preparation of active ingredients

EXAMPLE 1

Chloro-ethoxy-myristato-aluminum (according to process A)

A solution of 4.75 g (103.2 mmol) of absolute ethanol in 150 ml of absolute n-hexane is added dropwise at 0° C. and while stirring during about half an hour to a solution of 18.24 g (103.2 mmol) of diisobutylaluminum chloride in 150 ml of absolute n-hexane at 0° C. and under a protective gas atmosphere (argon). Thereafter, the temperature of the mixture is allowed to rise to room temperature and the mixture is warmed at about 50° C. for about a further 1 hour to yield the chloro-ethoxy-isobutyl-aluminum starting material.

After subsequently cooling this mixture to 10° C., there is added dropwise during about half and hour a solution of 23.52 g (103.2 mmol) of myristic acid in 300 ml of absolute n-hexane. The temperature of the reaction mixture is allowed to rise to room temperature and the n-hexane is distilled off in vacuo. The remaining n-hexane is distilled off at 50° C. under reduced pressure by means of an oil pump. Chloro-ethoxy-nyristato-aluminum separates as a light yellowish colored resinous product; yield 33.8 g (97.8%).

|  | Microanalysis ($C_{16}H_{32}O_3ClAl$): | | |
|---|---|---|---|
|  | % C | % H | % Cl |
| Calculated: | 57.39 | 9.63 | 10.39 |
| Found: | 57.13 | 9.65 | 10.55 |

A molecular weight determination of this product gave, according to the diffusion method with a 0.508% solution in benzene, a molecular weight of about 3200. With a molecular weight 335 for the monomer, the value of 3200 gives an average degree of oligomerization of 9–10 molecules for the associated material.

EXAMPLE 2

Chloro-ethoxy-myristato-aluminum [according to process (B)]

Preparation of the subject compound is carried out analogously to the process described in Example 1 with the exception that myristic acid solution (to produce the chloro-isobutyl-myristato-aluminum starting material) is added first to the diisobutylaluminum chloride in the n-hexane solution and thereafter the ethanol solution. There is thus obtained the product of Example 1. The yield and purity are comparable with those of the Example 1 product.

EXAMPLE 3

Chloro-ethoxy-myristato-aluminum (according to process C)

19.8 g (100 mmol) of triisobutylaluminum are added dropwise and while stirring during half an hour at −10° C. to 200 ml of absolute diethyl ether under a protective gas atmosphere. Thereafter, the dropping funnel is rinsed twice with 25 ml of absolute diethyl ether each time and there is added dropwise to the flask contents a solution of 4.60 g (100 mmol) of absolute ethanol in 50 ml of absolute diethyl ether. The temperature of the mixture is allowed to rise to room temperature and the mixture is stirred at this temperature for an additional 1 hour. Then there is added dropwise during half an hour at about 10° C. a solution of 22.79 g (100 mmol) of myristic acid in 150 ml of absolute diethyl ether and the mixture is subsequently stirred for an additional 1 hour at room temperature to yield the ethoxy-isobutyl-myristato-aluminum starting material.

After cooling the mixture to 0° C., there are added dropwise thereto 100 ml of a 1-molar ethereal hydrochloric acid solution (100 mmol of HCl), which has been freshly prepared shortly before by introducing dry hydrogen chloride into cooled absolute diethyl ether, titrating to determine the HCl content and diluting to a content of 1 mol of HCl/l. The dropping funnel is rinsed out twice with 25 ml of absolute diethyl ether each time, the temperature of the mixture is allowed to rise to room temperature and the mixture is thereafter warmed at reflux temperature for 1 hour.

The diethyl ether is distilled off firstly in a water-jet vacuum, then by means of an oil pump and finally while warming to 50° C. There is thus obtained the product of Example 1. The yield and purity are comparable with those of the Example 1 product.

EXAMPLE 4

Chloro-ethoxy-myristato-aluminum (according to process D)

A solution of 4.75 g (103.2 mmol) of absolute ethanol in 100 ml of absolute n-hexane is added dropwise during half an hour while stirring at 0° C. and under a protective gas atmosphere (argon) to a solution of 9.12 g (51.6 mmol) of diisobutylaluminum chloride in 100 ml of absolute n-hexane in a four-necked flask. Thereafter, the mixture is warmed at 50° C. for about 1 hour and subsequently allowed to cool to room temperature. In this manner there is obtained the diethoxyaluminum chloride starting material.

Dimyristatolaluminum chloride is prepared in a second four-necked flask in an analogous manner from 9.12 g (51.6 mmol) of diisobutylaluminum chloride in 100 ml of absolute n-hexane and 23.52 g (103.2 mmol) of myristic acid in 300 ml of absolute n-hexane.

The solution of the diethoxyaluminum chloride formed in the first flask is transferred while excluding moisture into the dropping funnel of the second flask. During about half an hour the solution in the dropping funnel is dropped into the second solution and the mixture is warmed at reflux temperature for 4 hours. After cooling to room temperature, the mixture is worked-up as described in Example 1. There is thus obtained the product of Example 1. The yield and purity are comparable with those of the Example 1 product.

EXAMPLE 5

Chloro-ethoxy-myristato-aluminum (according to process E)

The aluminum triethylate and aluminum trimyristate required as the starting materials are prepared in accordance with the following equations:

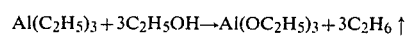

and

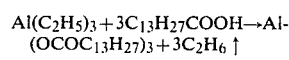

by adding a n-hexane solution of ethanol or of myristic acid to a n-hexane solution of triethylaluminum. After removing the solvent, the product is obtained almost quantitatively and analytically pure.

5.58 g (34.4 mmol) of aluminum triethylate, 24.40 g (34.4 mmol) of aluminum trimyristate and 4.59 g (34.4 mmol) of anhydrous aluminum trichloride are added to 400 ml of absolute toluene. The two first-named compounds and part of the aluminum trichloride dissolved upon stirring at room temperature. The remaining aluminum chloride dissolves after stirring for 1½ hours and warming at 60° C. The mixture is stirred for 12 hours at room temperature and the toluene is subsequently distilled off by means of an oil pump, finally at 50° C. to constant weight. There is thus obtained the product of Example 1. The yield and purity are comparable with those of the Example 1 product.

EXAMPLE 6

Chloro-ethoxy-benzoato-aluminum (according to process A)

A solution of 23.75 g (0.516 mol) of absolute ethanol in 350 ml of absolute toluene is added dropwise during 1 hour to a solution of 91.1 g (0.516 mol) of diisobutylaluminum chloride in 350 ml of absolute toluene at 0° C. and under a protective gas atmosphere (argon). Thereafter, the mixture is warmed at 50° C. for 1 hour and cooled to 5° C., to yield the chloro-ethoxy-isobutyl-aluminum starting material.

62.95 g (0.516 mol) of benzoic acid are added proportionwise (in each case about 5 g portions) to the mixture at 5° C. with continuous stirring. With the last addition the hitherto clear solution becomes turbid with the formation of a fine white precipitate. The mixture is stirred for 12 hours at room temperature, then warmed at 60° C. for 2 hours and the toluene is distilled off by means of an oil pump, finally at 30°–40° C. The precipitated fine white powder is dried to constant weight under reduced pressure (3 days at 70° C./1 mm). There are obtained 112.8 g of chloro-ethoxy-benzoato-aluminum; yield 95.6%; m.p. 270° C. with decomposition.

| | Microanalysis ($C_9H_{10}O_3ClAl$): | | | |
|---|---|---|---|---|
| | % C | % H | % Cl | % Al |
| Calculated: | 47.29 | 4.41 | 15.51 | 11.81 |
| Found | 47.24 | 4.62 | 15.26 | 11.76 |

EXAMPLE 7

Chloro-ethoxy-benzoato-aluminum (according to process F)

6.81 g (100 mmol) of sodium ethylate (prepared shortly before use by dissolving 2.3 g of sodium in about 100 ml of ethanol while cooling, distilling off the excess ethanol and drying the product in vacuo) and 14.41 g (100 mmol) of sodium benzoate are added to 300 ml of absolute diethyl ether under a protective gas atmosphere (argon). While stirring and cooling there is then added dropwise at 0° C. during 10 minutes a solution of 13.34 g (100 mmol) of anhydrous aluminum trichloride in 250 ml of absolute diethyl ether. Thereafter, the mixture is heated at reflux temperature for 1 hour. After cooling to room temperature, the product is decanted and the residual product is removed by repeatedly washing the apparatus and glass beads present therein with absolute diethyl ether. The mixture is filtered and the filter cake is washed several times with distilled water in portions of about 100 ml until the rinsings are chloride-free (3–4 washings). The filter cake is subsequently dried at 40° C. to constant weight over phosphorus pentoxide and under reduced pressure ($10^{-1}$ mm). In this manner there are obtained 17.95 g (78.5% yield) of chloro-ethoxy-benzoato-aluminum. The purity is comparable with that of the Example 6 product.

EXAMPLES 8–23

The appropriate starting materials of formulae II and III are reacted analogously to the process described in Example 1 (process A) to give the compounds of formula I listed in Table I hereinafter.

TABLE I $$R^1O-Al\begin{matrix}Cl\\ \\OCOR^2\end{matrix} \quad I$$

| Example | Starting material of formula II | Starting material of formula III | Compound of formula I R¹ | R² | Melting point °C. | Microanalysis (calculated/found) % C | % H | % Cl | % Al |
|---|---|---|---|---|---|---|---|---|---|
| 8 | Chloro-n-hexadecyloxy-isobutyl-aluminum | Myristic acid | n-$C_{16}H_{33}$ | n-$C_{13}H_{27}$ | | 67.83 / 67.92 | 11.38 / 11.39 | 6.67 / 6.71 | — |
| 9 | Chloro-(2-phenoxy-ethoxy)-isobutyl-aluminum | Benzoic acid | $C_6H_5OCH_2CH_2$ | $C_6H_5$ | 194° (with decomposition) | 56.18 / 56.30 | 4.40 / 4.48 | 11.05 / 10.96 | — |
| 10 | Chloro-phenoxy-isobutyl-aluminum | Myristic acid | $C_6H_5$ | n-$C_{13}H_{27}$ | | 62.74 / 62.94 | 8.42 / 8.67 | 9.26 / 9.38 | 7.04 / 7.12 |
| 11 | Chloro-phenoxy-isobutyl-aluminum | Nicotinic acid | $C_6H_5$ | 3-Pyridyl | | 51.91 / 51.38 | 3.27 / 3.28 | 12.77 / 13.03 | 9.72 / 9.83 |
| 12 | Chloro-n-hexadecyloxy-isobutyl-aluminum | Benzoic acid | n-$C_{16}H_{33}$ | $C_6H_5$ | | 65.00 / 64.82 | 9.01 / 9.44 | 8.34 / 8.68 | — |
| 13 | Chloro-ethoxy-isobutyl-aluminum | p-Methoxybenzoic acid | $C_2H_5$ | p-$CH_3OC_6H_4$ | >250° | 46.44 / 46.41 | 4.68 / 4.95 | — | 10.43 / 10.28 |
| 14 | Chloro-ethoxy-isobutyl-aluminum | p-Chlorobenzoic acid | $C_2H_5$ | p-Cl—$C_6H_4$ | >250° | 41.09 / 41.04 | 3.45 / 3.64 | — | 10.26 / 10.03 |
| 15 | Chloro-(2-methoxy-ethoxy)-isobutyl-aluminum | Benzoic acid | $CH_3OCH_2CH_2$ | $C_6H_5$ | >300° | 46.44 / 46.19 | 4.68 / 4.55 | — | 10.43 / 10.61 |
| 16 | Chloro-octyloxy-isobutyl-aluminum | Myristic acid | n-$C_8H_{17}$ | n-$C_{13}H_{27}$ | | 63.06 / 63.34 | 10.58 / 10.67 | 8.46 / 8.28 | — |
| 17 | Chloro-ethoxy-isobutyl-aluminum | o-Acetyloxybenzoic acid | $C_2H_5$ | o-$CH_3COOC_6H_4$ | >270° | 46.09 / 45.69 | 4.22 / 4.13 | 12.37 / 11.97 | — |
| 18 | Chloro-(2-phenoxy-ethoxy)-isobutyl-aluminum | Myristic acid | $C_6H_5OCH_2CH_2$ | n-$C_{13}H_{27}$ | | 61.89 / 61.85 | 8.50 / 8.87 | 8.30 / 8.20 | — |
| 19 | Chloro-ethoxy-isobutyl-aluminum | Nicotinic acid | $C_2H_5$ | 3-Pyridyl | >275° | 41.85 / 41.31 | 3.95 / 3.80 | — | 11.75 / 11.71 |
| 20 | Chloro-ethoxy-isobutyl-aluminum | Phenylacetic acid | $C_2H_5$ | $C_6H_5CH_2$ | 118–119° | 49.50 / 49.13 | 4.99 / 5.13 | 14.61 / 14.47 | 11.12 / 10.99 |
| 21 | Chloro-(p-ethoxy-carbonyl-phenoxy)-isobutyl-aluminum | Benzoic acid | p-$C_2H_5OCOC_6H_5$ | $C_6H_5$ | from 220° (with decomposition) | 55.11 / 55.23 | 4.05 / 4.17 | 10.17 / 10.34 | — |
| 22 | Chloro-(p-ethoxy-carbonyl-phenoxy)-isobutyl-aluminum | Myristic acid | p-$C_2H_5OCOC_6H_4$ | n-$C_{13}H_{27}$ | 132–133° | 60.72 / 60.54 | 7.98 / 8.13 | — | 5.93 / 5.90 |
| 23 | Chloro-ethoxy-isobutyl-aluminum | o-Methoxycarbonyl-benzoic acid | $C_2H_5$ | o-$CH_3OCOC_6H_4$ | 175–178° | 46.09 / 45.92 | 4.22 / 4.36 | 12.37 / 12.49 | 9.41 / 9.30 |

II. Formulation Examples

EXAMPLE 24

An antiperspirant spray has the following composition:

| | |
|---|---|
| Active substance of formula I (e.g. chloro-ethoxy-benzoato-aluminum) | 6.00 g |
| Isopropyl myristate | 5.80 g |
| Amorphous silicon dioxide | 0.20 g |
| Propellant gas [e.g. mixture of trichlorofluoromethane and dichlorodifluoromethane (60:40)] | 88.00 g |

The suspension of the active substances consisting of the above ingredients is filled into a metal aerosol can.

EXAMPLE 25

An antiperspirant spray has the following composition:

| | |
|---|---|
| Active substance of formula I [e.g. chloro-ethoxy-benzoato-aluminum] | 5.00 g |
| Absolute ethanol | 20.00 g |
| Propellant gas [e.g. mixture of trichlorofluoromethane and dichlorodifluoromethane (60:40)] | 75.00 g |

The solution consisting of the above ingredients is filled into a glass aerosol flask.

EXAMPLE 26

An antiperspirant spray has the following composition:

| | |
|---|---|
| Active substance of formula I [e.g. chloro-ethoxy-benzoato-aluminum] | 5.00 g |
| Absolute ethanol | 95.00 g |
| Perfume | optional amount |

The solution consisting of the above ingredients is filled into a plastic hand-spray flask.

EXAMPLE 27

An antiperspirant stick (waxy) has the following composition:

| | |
|---|---|
| Active substance of formula I [e.g. chloro-ethoxy-benzoato-aluminum] | 20.00 g |
| Stearyl alcohol | 30.00 g |
| Silcone oil (boiling point 190-200° C.) | 50.00 g |

The above ingredients are mixed with one another, melted and poured into sticks while stirring vigorously.

EXAMPLE 28

An antiperspirant stick (dry) has the following composition:

| | |
|---|---|
| Active substance of formula I [e.g. chloro-ethoxy-benzoato-aluminum] | 25.00 g |
| Talc | 9.00 g |
| Microcrystalline cellulose | 65.75 g |
| Magnesium stearate | 0.25 g |

The above ingredients are thoroughly mixed together and formed into sticks by an isostatic press process.

EXAMPLE 29

An antiperspirant gel has the following composition:

| | |
|---|---|
| Active substance of formula I [e.g. chloro-ethoxy-benzoato-aluminum] | 5.00 g |
| Absolute ethanol | 94.00 g |
| Cellulose polyalkyl ether | 1.00 g |

The above ingredients are mixed to form the gel.

III. Biological results

EXAMPLE 30

The testing of the compounds of formula I of this invention as active ingredients for antiperspirant compositions is carried out according to the Pads method which is described fully, e.g. in J. Invest. Dermatol. 43, 363-378 (1964), J. Soc. Cosmet. Chem. 23, 22-43 (1972) and Acta Dermatovener (Stockholm), 55, 241-260 (1975). In the test one armpit of the volunteers (in each case 1-13 persons) is treated with 2 ml of the suitable application form, e.g. solution or spray of fixed active ingredient concentration of the particular active ingredient. The other armpit is untreated and serves as the control.

The results are recorded in the following Table II:

TABLE II

| Compound of formula I (Example No.) | Concentration (weight percent) and solvent | Number of volunteers | Sweat reduction (average value) |
|---|---|---|---|
| Chloro-ethoxy-myristato-aluminum (1-5) | 10% in absolute ethanol | 3 | 56.1% |
| | 10% in absolute ethanol | 4 | 56.5% |
| Chloro-n-hexadecyloxy-myristato-aluminum (8) | 20% in absolute ethanol | 13 | 18.5% |
| Chloro-ethoxy-benzoato-aluminum (6,7) | 22% in absolute ethanol | 4 | 74.8% |
| Chloro-(2-phenoxyethoxy)-benzoato-aluminum (9) | 20% in rectified alcohol | 5 | 67.4% |
| Chloro-ethoxy-(p-methoxyphenyl)-aluminum (13) | 20% in absolute ethanol | 4 | 43.9% |
| Chloro-ethoxy-(o-acetyloxy-benzoato)-aluminum (17) | 20% in rectified alcohol | 4 | 46.0% |
| Chloro-(2-phenoxy-ethoxy)-myristato-aluminum (18) | 20% in rectified alcohol | 4 | 39.3% |
| Chloro-ethoxy-phenylacetoato-aluminum (20) | 20% in absolute ethanol | 1 | 77.4% |
| Chloro-n-hexadecycloxy-benzoato-aluminum (12) | 20% in absolute ethanol | 4 | 32.2% |

We claim:

1. A compound of the formula

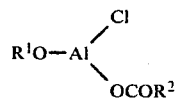

wherein $R^1$ is $C_{1-18}$-alkyl, $C_{2-18}$-alkoxyalkyl, phenoxy-$C_{1-6}$-alkyl, phenyl or phenyl substituted with $C_{2-6}$-alkoxycarbonyl and $R^2$ is $C_{1-15}$-alkyl; phenyl or phenyl substituted with halogen, $C_{1-4}$-alkyl, $C_{1-4}$-alkoxy, $C_{2-6}$-alkanoyloxy and/or $C_{2-6}$-alkoxycarbonyl; phenyl-$C_{1-4}$-alkyl; or pyridyl.

2. The compound of claim 1, wherein $R^1$ is $C_{1-18}$-alkyl or phenoxy-$C_{1-6}$-alkyl.

3. The compound of claim 1 or claim 2, wherein $R^2$ is $C_{1-15}$-alkyl, phenyl or phenyl substituted with halogen, $C_{1-4}$-alkyl, $C_{1-4}$-alkoxy, $C_{2-6}$-alkanoyloxy and/or $C_{2-6}$-alkoxycarbonyl, or phenyl-$C_{1-4}$-alkyl.

4. Chloro-ethoxy-benzoato-aluminum.

5. Chloro-ethoxy-myristato-aluminum.

6. Chloro-(2-phenoxy-ethoxy)-benzoato-aluminum.

7. Chloro-ethoxy-phenylacetoato-aluminum.

8. A compound according to claim 1 selected from the group consisting of:

Chloro-n-hexadecyloxy-myristato-aluminum,
chloro-phenoxy-myristato-aluminum,
chloro-phenoxy-nicotinoyloxy-aluminum,
chloro-n-hexadecyloxy-benzoato-aluminum,
chloro-ethoxy-p-methoxybenzoato-aluminum,
chloro-ethoxy-p-chlorobenzoato-aluminum,
chloro-(2-methoxyethoxy)-benzoato-aluminum,
chloro-octyloxy-myristato-aluminum,
chloro-ethoxy-o-acetyloxybenzoato-aluminum,
chloro-(2-phenoxyethoxy)-myristato-aluminum,
chloro-ethoxy-nicotinyloxy-aluminum,
chloro-(p-ethoxycarbonyl-phenoxy)-benzoato-aluminum,
chloro-(p-ethoxycarbonyl-phenoxy)-myristato-aluminum and
chloro-ethoxy-o-methoxycarbonylbenzoato-aluminum.

9. An antiperspant composition comprising an effective amount of at least one compound of the formula

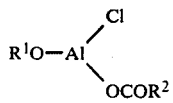

wherein
R$^1$ is C$_{1-18}$-alkyl, C$_{2-18}$-alkoxyalkyl, phenoxy-C$_{1-6}$-alkyl, phenyl or phenyl substituted with C$_{2-6}$-alkoxycarbonyl and
R$^2$ is C$_{1-15}$-alkyl; phenyl or phenyl substituted with halogen, C$_{1-4}$-alkyl, C$_{1-4}$-alkoxy, C$_{2-6}$-alkanoyloxy and/or C$_{2-6}$-alkoxycarbonyl; phenyl-C$_{1-4}$-alkyl; or pyridyl,
as well as carrier material customary in cosmetics or other cosmetically-effective adjuvant.

10. An antiperspirant composition according to claim 9, wherein the active ingredient is chloro-ethoxy-benzoato-aluminum.

11. An antiperspirant composition according to claim 9, wherein the active ingredient is chloro-ethoxy-myristato-aluminum.

12. An antiperspant composition according to claim 9, wherein the active ingredient is chloro-(2-phenoxyethoxy)-benzoato-aluminum.

13. An antiperspirant composition according to claim 9, wherein the active ingredient is chloro-ethoxy-phenylacetoato-aluminum.

14. A method for inhibiting transpiration, comprising applying an effective amount of antiperspirant composition according to claim 9, 10, 11, 12 or 13 to the area to be treated.

* * * * *